United States Patent
Castellano Orozco et al.

(10) Patent No.: US 12,245,623 B2
(45) Date of Patent: Mar. 11, 2025

(54) OLIVE OIL ENRICHED WITH OLEANOLIC ACID, PROCESS FOR ITS PREPARATION AND USE THEREOF

(71) Applicants: CONSEJO SUPERIOR DE INVESTIGACIONES CIENTÍFICAS (CSIC), Madrid (ES); SERVICIO ANDALUZ DE SALUD, Seville (ES)

(72) Inventors: Jose Maria Castellano Orozco, Seville (ES); Mirela Rada, Seville (ES); Angeles Guinda Garin, Seville (ES); Jose Manuel Santos Lozano, Seville (ES); Jose Lapetra Peralta, Seville (ES)

(73) Assignees: CONSEJO SUPERIOR DE INVESTIGACIONES CIENTÍFICAS (CSIC), Madrid (ES); SERVICIO ANDALUZ DE SALUD, Seville (ES)

( * ) Notice: Subject to any disclaimer, the term of this patent is extended or adjusted under 35 U.S.C. 154(b) by 993 days.

(21) Appl. No.: 17/258,588

(22) PCT Filed: Jul. 8, 2019

(86) PCT No.: PCT/EP2019/068199
§ 371 (c)(1),
(2) Date: Jan. 7, 2021

(87) PCT Pub. No.: WO2020/011689
PCT Pub. Date: Jan. 16, 2020

(65) Prior Publication Data
US 2021/0227867 A1    Jul. 29, 2021

(30) Foreign Application Priority Data

Jul. 9, 2018 (EP) .................................. 18382510

(51) Int. Cl.
*A23L 33/115* (2016.01)
*A61K 9/00* (2006.01)
(Continued)

(52) U.S. Cl.
CPC .......... *A23L 33/115* (2016.08); *A61K 9/0053* (2013.01); *A61K 9/10* (2013.01);
(Continued)

(58) Field of Classification Search
None
See application file for complete search history.

(56) References Cited

FOREIGN PATENT DOCUMENTS

CN    103356480 A    10/2013
EP     1013752 A1    6/2000
(Continued)

OTHER PUBLICATIONS

CN103356480A—Google English Translation (Year: 2014).*
(Continued)

*Primary Examiner* — Kyung S Chang
(74) *Attorney, Agent, or Firm* — Hayes Soloway PC (57) ABSTRACT

The present invention relates to an olive oil enriched with oleanolic acid that comprises a concentration of oleanolic acid between 580 and 650 mg/kg. This functional olive has proven to be effective in the treatment and prevention of type 2 Diabetes Mellitus and pre-diabetes. Also, the invention relates to a process for the preparation of said functional olive oil enriched with oleanolic acid.

11 Claims, 3 Drawing Sheets

(51) Int. Cl.
- A61K 9/10 (2006.01)
- A61K 31/56 (2006.01)
- A61K 36/63 (2006.01)
- A61P 3/10 (2006.01)
- B82Y 5/00 (2011.01)
- B82Y 40/00 (2011.01)

(52) U.S. Cl.
CPC .............. *A61K 31/56* (2013.01); *A61K 36/63* (2013.01); *A61P 3/10* (2018.01); *B82Y 5/00* (2013.01); *B82Y 40/00* (2013.01)

(56) References Cited

FOREIGN PATENT DOCUMENTS

| EP | 2305783 A1 | 4/2011 |
|---|---|---|
| ES | 2160553 A1 | 6/2002 |

OTHER PUBLICATIONS

Angeles Guinda, "Pentacyclic Triterpenoids from Olive Fruit and Leaf", Journal, 2010, 9685-9691, vol. 58, Journal of Agricultural and Food Chemistry.
M.C. Perez-Camino, "Quantitative Determination of Hydroxy Pentacyclic Triterpene Acids in Vegetable Oils", Journal, 1999, 1558-1562, vol. 47, Journal of Agricultural and Food Chemistry.
Hiye-Young Sung, "Oleanolic Acids Reduces Markers of Differentiation in 3T3-L1 Adipocytes", Journal, 2010, 831-839 Vol. 30, Nutrition Research.
Xiaoming Zhao, "Oleanolic Acid Suppresses the Proliferation of Lung Carcinoma Cells by miR-122/Cyclin G1/MEF2D Axis", Journal, 2015, 1-7, vol. 400, Molecular and Cellular Biochemistry.
American Diabetes Association, "Diagnosis and Classification of Diabetes Mellitus", Journal, 2010, S62-S69, vol. 33, Supp. 1, Diabetes Care.
Suneetha Amara, "Oleanolic Acid Inhibits High Salt Induced Exaggeration of Warburg-Like Metabolism in Breast Cancer Cells", Journal, 2016, 1-12, vol. 74, No. 3, Cell Biochemistry and Biophysics.
Nidhi Bansal, "Prediabetes Diagnosis and Treatment: A Review", Journal, 2015, 296-303, vol. 6, No., 2, World Journal of Diabetes.
Danielle Camer, "The molecular mechanisms underpinning the therapeutic properties of oleanolic acid, its isomer and derivatives for type 2 diabetes and associated complications", Journal, 2014, 1-25, vol. 58, No. 8, Molecular Nutrition and Food Research.
Jose M. Castellano, "Biochemical Basis of the Antidiabetic Activity of Oleanolic Acid and Related Pentacyclic Triterpenes", Journal, 2013, 1791-1799, vol. 62, Diabetes.
Meiwan Chen, "Recent Advances in Nanoparticle Formulation of Oleanolic Acid", Journal, 2011, 1-4, vol. 6, No. 20, Chinese Medicine.
Ramon Estruch, M.D., "Primary Prevention of Cardiovascular Disease with a Mediterranean Diet", Journal, 2013, 1279-1290, vol. 368, No. 14, The New England Journal of Medicine.
Dick De Zeeuw, M.D., "Bardoxolone Methyl in Type 2 Diabetes and Stage 4 Chronic Kidney Disease", Journal, 2015, 1-16, vol. 369, No. 26, The New England Journal of Medicine.
Sebastian Jager, "Pentacyclic Triterpene Distribution in Various Plants—Rich Sources for a New Group of Multi-Potent Plant Extracts", Article, 2009, 2016-2031, vol. 14, Molecules.
Ming Li, "Oleanolic Acid Attenuates Insulin Resistance via NF-kB to Regulate the IRS1-GLUT4 Pathway in HepG2 Cells", Article, 2015, 1-9, vol. 2015, Evidence-Based Complementary and Alternative Medicine.
Jie Liu, "Pharmacology of Oleanolic Acid and Ursolic Acid", Journal, 1995, 57-68, vol. 49, Journal of Ethnopharmacology.
Ruben Martin, "Beneficial Actions of Oleanolic Acid in an Experimental Model of Multiple Sclerosis: a Potential Therapeutic Role", Manuscript of Journal, 2009, 1-43, vol. 79, No. 2, Biochemical Pharmacology.
Da-Wei Mu, "Oleanolic Acid Suppresses the Proliferation of Human Bladder Cancer at Akt/mTOR/S6K and ERK1/2 Signaling", Journal, 2015, 13864-13870, vol. 8, No. 11, International Journal of Clinical and Experimental Pathology.
Pablo E Pergola, "Bardoxolone Methyl and Kidney Function in CKD with Type 2 Diabetes", Journal, 2011, 1-11, vol. 365, No. 4, The New England Journal of Medicine.
Omid Rad Pour, "Prediabetes as a Therapeutic Target", Journal, 2011, 1-12, vol. 57, No. 2, Clinical Chemistry.
Mirela Rada, "GC-FID Determination and Pharmacokinetic Studies of Oleanolic Acid in Human Serum", Journal, 2015, 1-16, vol. 29, No. 11, Biomedical Chromatography.
Miguel Angel Rodriguez Chamorro, "Revisión de tests de medición del cumplimiento terapéutico utilizados en la práctica clinica", Journal, 2008, 413-417, vol. 40, No. 8, Aten Primaria.
Piotr Ruszkowski, "Natural Triterpenoids and their Derivatives with Pharmacological Activity Against Neurodegenerative Disorders", Article, 2014, 307-315, vol. 11, Mini-Reviews in Organic Chemistry.
Jordi Salas-Salvado, "Prevention of Diabetes with Mediterranean Diets a Subgroup Analysis of a Randomized Trial", Article, 2014, 1-27, vol. 160, Annals of Internal Medicine.
L Schwingshackl, "Olive oil in the prevention and management of type 2 diabetes mellitus: a systematic review and meta-analysis of cohort studies and intervention trials", Article, 2017, 1-6, vol. 7, Nutrition and Diabetes.
Xin Wang, "Inhibitory effect of oleanolic acid on hepatocellular carcinoma via ERK-p53-mediated cell cycle arrest and mitochondrial-dependent apoptosis", Journal, 2013, 1323-1330, vol. 34, No. 6, Carcinogensis.
Yan-Yang Wang, "Bardoxolone Methyl (CDDO-Me) as a Therapeutic Agent: an Update on its Pharmacokinetic and Pharmacodynamic Properties", Journal, 2014, 2075-2088, vol. 8, Drug Design, Development and Therapy.
Wenji Li, "Development and Evaluation of Optimized Sucrose Ester Stabilized Oleanolic Acid Nanosuspensions Prepare by Wet Ball Milling with Design of Experiments", Article, 2014, 326-937, vol. 37, No. 6, Biological and Pharmaceutical Bulletin.
Rui Yang, "Self-Microemulsifying Drug Delivery System for Improved Oral Bioavailability of Oleanolic Acid: Design and Evaluation", Journal, 2013, vol. 8, 2917-2926, International Journal of Nanomedicine.
Ki-Yeol Yoo, "Terpenoids as Potential Anti-Alzheimer's Disease Therapeutis", Journal, 2012, 3524-3538, vol. 17, Molecules.

\* cited by examiner

OLIVE OIL ENRICHED WITH OLEANOLIC ACID, PROCESS FOR ITS PREPARATION AND USE THEREOF

CROSS-REFERENCE TO RELATED APPLICATIONS AND PRIORITY

This patent application claims priority from PCT Patent Application No. PCT/EP2019/068199 filed Jul. 8, 2019, which claims priority from European Patent Application No. 18382510.8 filed Jul. 9, 2018. Each of these patent applications are herein incorporated by reference in its/their entirety.

The invention relates to a functional olive oil enriched with oleanolic acid, whose intake at the specified dose has proven to be effective in the prevention of prediabetes and type 2 Diabetes Mellitus. Also, the invention relates to a process for the preparation of said functional olive oil enriched with oleanolic acid.

BACKGROUND ART

Type 2 Diabetes Mellitus (DM2) is a metabolic disease of multiple etiology, characterized by chronic hyperglycemia with impaired carbohydrate, lipid and protein metabolisms. Its prevalence is increasing dramatically in recent years due to the aging of population and changes in the lifestyle that lead to unhealthy nutrition, sedentary lifestyle, and overweight/obesity. According to WHO, the global prevalence of diabetes in adults has increased from 4.7% in 1980 to 8.5% in 2014. DM2 affected more than 422 million people worldwide in 2014, and it is estimated that the number of affected individuals will continue growing, reaching 592 million people in 2030. At present, a 40.5% of the diabetic population is unaware that they suffer DM2, since the symptoms appear when the disease already seriously damage organs and vital functions, diminishing the quality of life and reducing the life expectancy of those who suffer from it. In 2013, diabetes was directly or indirectly responsible for 5.1 million deaths worldwide. The scenario is even more worrying by the burst of new cases of DM2 in young people. The incidence of this disease in children and adolescents increases each year at an average rate of 3.9%. If trend continues, the number of diabetic children in 2020 will have practically doubled compared to the data reported in 2005.

There is a growing interest in obtaining natural bioactive compounds for the treatment of diabetes and its previous stages of development.

Figure 1:
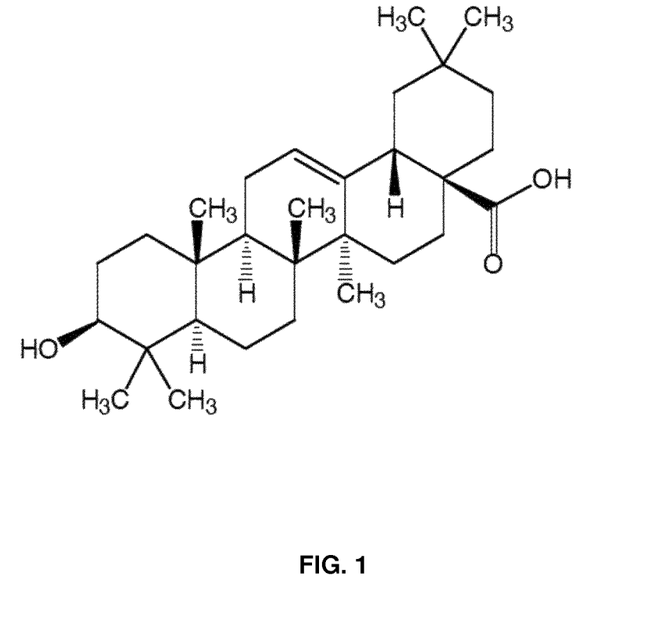
FIG. 1. Chemical structure of oleanolic acid.

Oleanolic acid is a plant secondary metabolite, widely distributed in the plant kingdom as free acid or aglycone of triterpenoid saponins (Jäger S. et al. Pentacyclic triterpene distribution in various plants—rich sources for a new group of multi-potent plant extracts. Molecules 2009; 14: 2016-2031). Oleanolic acid (OA; 3b-hydroxy-olean-12-en-28-oic acid) (FIG. 1) has been described in more than 200 plant species, being especially abundant in the olive (*Olea europaea* L.), as component of the cuticle waxes that cover fruit and leaf epidermis (Guinda A, et al. Pentacyclic triterpenoids from olive fruit and leaf. J Agric Food Chem 2010; 58:9685-9691). Therefore, it is also a natural component of olive oils (Pérez-Camino, M C. et al. Quantitative Determination of Hydroxy Pentacyclic Triterpene Acids in Vegetable Oils. *J. Agric. Food Chem.* 1999, 47, 1558-1562). OA is mainly concentrated as free acid in the olive leaf, where it may become represent a 3.5% of the leaf dry matter (Guinda A. et al. Pentacyclic triterpenoids from olive fruit and leaf. J Agric Food Chem 2010; 58:9685-9691).

OA is increasingly endowed with a wide range of biological activities with potential effects on health, which include antioxidant, microbicide, anti-inflammatory, hypolipidemic, hepatoprotective and cardioprotective effects (Liu J. Pharmacology of oleanolic acid and ursolic acid. *J Ethnopharmacol* 1995; 49:57-68; Dzubak P. et al. Pharmacological activities of natural triterpenoids and their therapeutic implications. *Nat Prod Rep* 2006; 23:394-411). In addition, it has demonstrated ability to interfere in the development of different types of cancer and neurodegenerative disorders (Wang, X. et al. Inhibitory effect of oleanolic acid on hepatocellular carcinoma via ERK-p53-mediated cell cycle arrest and mitochondrial-dependent apoptosis. Carcinogenesis 2013, 34, 1323-1330; Amara, S. et al. Oleanolic Acid Inhibits High Salt-Induced Exaggeration of Warburg-like Metabolism in Breast Cancer Cells. *Cell Biochem. Biophys.* 2016, 74, 427-434; Mu, D. W. et al. Oleanolic acid suppresses the proliferation of human bladder cancer by Akt/mTOR/S6K and ERK1/2 signaling. *Int. J. Clin. Exp. Pathol.* 2015, 8, 13864; Zhao, X. et al. Oleanolic acid suppresses the proliferation of lung carcinoma cells by miR-122/Cyclin G1/MEF2D axis. *Mol. Cell. Biochem.* 2015, 400, 1-7; Martin R. et al. Beneficial actions of oleanolic acid in an experimental model of multiple sclerosis: a potential therapeutic role. *Biochem Pharmacol* 2010; 79:198-208; Yoo K-Y. et al. Terpenoids as potential anti-Alzheimer's disease therapeutics. *Molecules* 2012, 17, 3524-5338; Ruszkowski P, Bobkiewicz-Kozlowska T. Natural triterpenoids and their derivatives with pharmacological activity against neurodegenerative disorders. *Mini-Reviews in Organic Chemistry* 2014, 11, 307-315).

Also, the antidiabetic action of OA has been approached in the last years (Li, M. et al. Oleanolic Acid Attenuates Insulin Resistance via NF-κB to regulate the IRS1-GLUT4 Pathway in HepG2 Cells. Evid. Based Complement. Altern. Med. 2015, 2015, 643102).

These OA properties have been demonstrated in experimental research models, but studies in human are surprisingly almost non-existent. A reason of that was likely the assumption that OA had poor bioavailability. In fact, it is practically insoluble in aqueous media, but partially soluble in lipophilic matrices.

In the last two decades, organic chemists have created more than 300 OA derivatives, trying to produce synthetic triterpenoids more active than OA itself against both the inflammatory and oxidative stresses involved in many human diseases. The most notorious derivative likely is 2-cyano-3,12-dioxooleana-1,9(11)-dien-28-oic acid (CDDO) methyl ester (bardoxolone methyl). Bardoxolone methyl showed promising effects for the treatment of chronic kidney diseases (CKD), cancer (lymphoma and solid tumors), and pulmonary arterial hypertension (Wang Y-Y, Yang Y-X, Zhe H, He Z-X, Zhou S-F. Bardoxolone methyl (CDDO-Me) as a therapeutic agent: An update on its pharmacokinetic and pharmacodynamic properties. Drug Design, Development and Therapy 2014, 8, 2075-2088), but displayed common adverse effects such as fatigue, nausea, anorexia, muscle spasm, mild elevations in alanine aminotransferase levels and gastrointestinal disarrays [Pergola P E, Raskin P, Toto R D, Meyer C J, Huff μW, Grossman E B, Krauth M, Ruiz S, Audhya P, Christ-Schmidt H, Wittes J, Warnock D G Bardoxolone methyl and kidney function in CKD with type 2 diabetes. N. Engl. J. Med. 2011, 365, 327-336] However, the safety of CDDO-Me is seriously questioned nowadays. The BEACON Study (Bardoxolone Methyl Evaluation in Patients with Chronic Kidney Disease and Type 2 Diabetes; NCT01351675) was halted 16 months after its onset, since patients treated with CDDO-Me experienced a higher rate of heart-related adverse events, including heart failure and death (de Zeeuw D, Akizawa T, Audhya P, Bakris G L, Chin M, Christ-Schmidt H, Goldsberry A, Houser M, Krauth M, Lambers-Heerspink H J, McMurray J J, Meyer C J, Parving H-H, Remuzzi G, Toto R D, Vaziri N D, Wanner C, Wittes J, Wrolstad D, Chertow G M. Bardoxolone methyl in type 2 diabetes and stage 4 chronic kidney disease. N. Engl. J. Med. 2013, 369, 2492-2503).

Drugs used for the treatment of diabetes mellitus, like almost all, can also produce adverse effects. At present, one of the most commonly used agents is metformin (a biguanide), for which gastrointestinal intolerance (diarrhea, nausea, abdominal pain) has been described as the most common adverse effect. More serious effects have also been reported, such as the possibility of causing vitamin B12 deficiency or the appearance of lactic acidosis. On the other hand, thiazolidinediones (rosiglitazone, troglitazone and pioglitazone) can produce hydrosaline retention, while alpha-glucosidase inhibitors (acarbose and miglitol) can cause gastrointestinal discomfort, such as flatulence, abdominal distension, nausea or alteration of the depositional habit.

Clinical observations indicate that DM2 is preceded by a dysglycemia period, known as pre-diabetes, during which only specific diagnostic symptoms are manifested (Pour O R. et al. Prediabetes as a therapeutic target. *Clinical Chemistry* 2011, 57, 215-220). Pre-diabetes involves impaired fasting glucose (IFG) and impaired glucose tolerance (IGT). IFG is related with impaired fasting insulin secretion and the loss of control of hepatic glucose output, whereas IGT involves the inadequate beta-cell secretory response and abnormalities in hepatic and peripheral insulin sensitivity. Both IFG and IGT are cumulative risk factors to develop diabetes at short time (Bansal N. Prediabetes diagnosis and treatment: A review. World J Diabetes 2015, 15, 296-303).

The use of functional foods or drugs containing natural OA that produce its pharmacological action in absence of adverse effects could be a new and interesting strategy against diabetes and its previous stages of development. Based on the pharmacological potential of this triterpene, the present invention provides a functional olive oil enriched with oleanolic acid that is effective in the primary prevention of diabetes.

SUMMARY OF THE INVENTION

The present invention discloses a novel composition based in olive oil enriched with oleanolic acid.

Therefore, a first aspect of the present invention relates to olive oil enriched with oleanolic acid (OA), characterized in that the concentration of OA in said olive oil is comprised between 580 and 650 mg/kg, preferably 600 mg/kg.

Preferably, the olive oil is virgin olive oil, extra virgin olive oil, refined olive oil, pomace olive oil or mixtures thereof.

The oleanolic acid of the enriched olive oil is of natural origin, not chemically modified. It is obtained from the olive leaf.

A second aspect of the present invention provides a process for the preparation of the olive oil enriched with OA as defined in the first aspect of the invention.

Firstly, the process requires the preparation of crystalized OA. Crystalized OA is obtained according to the procedure described in the document ES2160553B1, the procedure comprises the next steps:

a) extraction of oleanolic acid from the leaves of *Olea europaea* by contacting the leaves of *Olea europaea* with an organic solvent for a time comprised between 30 and 240 minutes in a leaf/solvent ratio comprised between 1/10-1/50 weight/volume and at a temperature comprised between 20° C.-70° C.;
b) filtration of the extract obtained in the previous stage;
c) concentration of the filtrate obtained in the previous step by evaporation of the solvent until achieving a volume comprised between 5% and 20% of the initial one before concentration;
d) Oleanolic acid was obtained by fractioned crystallization at room temperature (between 18 and 27° C., preferably between 23 and 25° C.), and separation of OA crystals was carried out by filtration;
e) drying of the crystalized solid separated in the previous step for a period of time comprised between 5 and 30 minutes and at a temperature comprised between 130° C. and 220° C.

In the present invention, in a preferred embodiment, the leaves of *Olea europaea* used in step a) to obtain the cristallyzed OA are dry leaves, and more preferably senescent dry leaves. So, in case of using dry leaves, the procedure includes a previous step of drying the leaves. The leaves are drying to constant weight using any known methodology by the expert in the state of the art, for example in oven using a temperature between 50 and 85° C., preferably 60° or under the sun.

The cystalized OA obtained initially in step e) has 95% purity, which can be increased up to 98% by the drying step, values considerably higher than other obtained OA, for example, extraction procedures Optionally, the leaves are washed and dried prior to extraction with organic solvent (for example, ethanol, methanol and ethyl acetate).

Drying the olive leaf, and preferably senescent dry olive leaf, allows, to delete the decoloring step also included in the document ES2160553B1, which further than minimizing losses of the product and solvent, makes the procedure more sustainable and environmental friendly.

Once the crystalized OA is prepared, at least the following steps are carried out:
1) grinding the crystalized OA to produce nanoparticles,
2) addition of OA nanoparticles to a portion of starting olive oil until a concentration between 6000 and 6600 mg/kg to form a nanosuspension,
3) the nanosuspension obtained in step b) is submitted to treatment by ultrasounds,
4) then, the nanosuspension obtained in step 3) is diluted between 1:7 and 1:15 with the starting olive oil (volume nanosuspension:volume starting olive oil) and then the obtained solution of OA in olive oil is stirred at temperature between 20 and 27° C., between 10 and 15 hours.

In a preferred embodiment, before adding the OA to the starting olive oil (that is, before step 2), the crystalized OA is grinded to obtain nanoparticles for 2.5 cycles of 10 min at 500 rpm, in a planetary micro mill, equipped with agathe balls (5-10 mm diameter) obtaining this way particles with an average size between 90-300 nm in the 70-95% by weight of the OA mass (of the total crystalized OA), more preferably between 140 y 250 nm in the 70-95%.

The starting olive oil can be a commercially available olive oil and it can be, for example, virgin olive oil, extra virgin olive oil, refined olive oil, pomace olive oil or mixtures thereof.

Preferably, the suspension obtained in step 2) is stirred for 15-30 min, at temperature between 20-27° C. and more preferably between 18-25° C.

In a preferred embodiment, the suspension obtained in step 2) has a total concentration of OA of 6000 mg/kg.

In a preferred embodiment, the ultrasounds of step 3) are carried out at 180 W, 38° C. for 15 min.

In a preferred embodiment, the step 3) is carried out without surfactants.

In a preferred embodiment, the step 4) is carried out in a container of stainless steel.

Preferably, the diluted suspension obtained in step 4) is stirred for 12 hours.

The higher solubilization of the grinded crystalized OA in the olive oil enriched with OA, allows a surprisingly great biodisponibillity of the OA. This solubilization avoids the need to dissolve the OA in an organic solvent (for example ethanol), that would be the more preferred way to add the OA to a lipidic matrix, in those cases where OA is being part of an extract. In those cases the organic solvent should be later eliminated by heating, which could negatively affect to the organoleptic properties of the oil.

Additionally to the naturally OA in free acid form, the oleanolic acid naturally formed as glycosylated derivatives and esters, is included in the scope of the present invention.

A third aspect of the present invention also relates to the olive oil enriched with oleanolic acid (OA) obtained by the method described above.

Another aspect of the invention relates to the olive oil enriched with oleanolic acid as defined in the first aspect of the invention for use as a medicament.

The olive oil enriched with OA obtained by the methods described above, keeps unaltered its excellent organoleptic properties.

In a preferred embodiment, the olive oil enriched with oleanolic acid is used in the prevention and/or treatment of Diabetes Mellitus type 2 and in the treatment of pre-diabetes.

In a preferred embodiment, the olive oil enriched with oleanolic acid is administered to a subject at a daily dose between 45 and 65 mL, more preferably 55 mL per day (since the functional oil is enriched up to 600 mg/kg in AO, it takes 55 mL for the contribution of 35-38 mg of the bioactive compound (OA)).

The present invention demonstrates that a daily administration of 55 mL of the olive oil as defined in the first aspect of the invention reduces the risk of type 2 diabetes mellitus in a 45.8% [HR 0.542 (IC95 0.300-0.979); p=0.043], in relation to commercial olive oils (olive oils not enriched with crystalized oleanolic acid).

The olive oil enriched with oleanolic has proven to provide the highest bioavailability for OA reported until now, and shown that its long-term administration is safe.

Preferably, the olive oil enriched with OA is administered orally.

Also, the present invention shows that OA bioavailability depends on the characteristics of the formulation in which it is administered, and that the solubilisation of the triterpene (AO) in olive oils is appropriate for the exploitation of its pharmacological capabilities.

The present invention also relates to a pharmaceutical composition comprising the olive oil enriched with oleanolic.

The pharmaceutical composition can comprise the olive oil enriched with oleanolic, as described above, and at least one excipient, adjuvant and/or a pharmaceutically acceptable carrier. Additionally, the pharmaceutical composition is envisaged to contain another main ingredient.

Pharmaceutical compositions containing a therapeutically effective amount of the olive oil enriched with oleanolic acid together with the pharmaceutically acceptable carriers, constitute an additional aspect of the present invention. It relates to a pharmaceutical composition comprising at least one pharmaceutically acceptable carrier and a therapeutically effective amount of the olive oil enriched with oleanolic acid.

The term "carrier" relates to a dilute, adjuvant or excipient with which the main ingredient (the olive oil enriched with oleanolic acid) is administered. Such pharmaceutical carriers may be sterile liquids, such as water and other oils, including those derived from oil, animal, vegetable or synthetic, such as peanut oil, soybean oil, mineral oil, sesame seed oil and similar.

The therapeutically effective amount of the olive oil enriched with oleanolic acid of the invention must be administered (also referred to herein as therapeutically amount effective thereof), in addition to their dosage for treating a pathological condition with said compounds, will depend on a number of factors, including age, the condition of the patient, the severity of the disease, administration route and frequency, the modular compound to be used, etc. But, preferably, therapeutically effective amount of the olive oil enriched with oleanolic acid is a daily dose between 45 and 65 mL The olive oil enriched with oleanolic acid of this invention can be used on their own or jointly with other drugs to provide combined therapy. The other drugs can form part of the same pharmaceutical composition or be provided as a separate pharmaceutical composition, to be administered simultaneously or at different intervals. Examples of pharmaceutical compositions include any solid composition (tablets, pills, capsules, granules, etc.) or liquid composition (solutions, suspensions or emulsions) for oral, topical or parenteral administration.

The olive oil enriched with OA can be administered in combination (separately, simultaneously or sequentially) with other medicaments for the prevention and/or treatment of Diabetes Mellitus type 2 or for the treatment of pre-diabetes.

The last aspect of the present invention relates to a food composition comprising the oil enriched with oleanolic acid (OA) as defined in the present invention.

As used herein, the term "average particle size" refers to a mean average particle size determined by Laser Diffraction Particle Size Analysis.

The term "nanoparticles" in the present invention refers to particles with an average particle size between 1 and 1000 nm, preferably between 90-300 nm more preferably between 140 y 250 nm.

The term "aggregate" as employed in the description is intended to include OA particles originated during the milling by aggregation of nanoparticles. Preferably aggregates have an average size of 3 μm approximately.

The terms "extra virgin olive oil", "virgin olive oil", "refined olive oil", and "olive pomace oil", are widely known in the art. Nevertheless, definitions by the International Olive Oil Council [document COI/T.15/NC no 3/Rev. 11 (July 2016)] and by the European Commission [Regulation (EEC) No 2568/91] are provided below for a greater clarity.

Virgin olive oils are those obtained from the fruit of the olive tree (*Olea europaea* L.) only by mechanical methods or by other physical means in conditions, especially thermal, that do not produce the alteration of the oil, and that has not had more treatment than the washing, decanting, centrifugation and filtering.

The term "extra virgin olive oil" refers to virgin olive oil whose free acidity expressed in oleic acid is a maximum of 0.8 grams per 100 grams and whose other physicochemical and organoleptic characteristics correspond to those set for this category.

The term "virgin olive oil" refers to virgin olive oil whose free acidity expressed in oleic acid is a maximum of 2.0% and whose other physicochemical and organoleptic characteristics correspond to those set for this category.

The term "refined olive oil" refers to olive oil obtained from virgin olive oils by refining techniques that do not cause any modification of the initial glyceride structure. Its free acidity expressed in oleic acid is a maximum of 0.3% and its other physicochemical and organoleptic characteristics correspond to those set for this category.

The term "olive pomace oil" refers the oil obtained by treatment with solvents or other physical procedures of olive pomace, excluding oils obtained by reesterification procedures and any mixture with oils of another nature. Commercial olive-pomace oil is that constituted by a mixture of refined olive-pomace oil and virgin olive oil suitable for consumption in the form in which they are obtained. Its free acidity expressed in oleic acid is at most 1%, and its other physicochemical and organoleptic characteristics correspond to those set for this category.

The term "pre-diabetes" as used herein refers to a condition in which blood glucose levels are higher than normal but are not high enough for a diagnosis of diabetes. People with pre-diabetes are at increased risk for developing Type 2 diabetes and for heart disease and stroke. Prediabetes includes the impaired fasting glucose (IFG) and/or impaired tolerance to glucose (ITG) stages. Diagnosis of prediabetes includes one of the following parameters: an HbA1c of 5.7%-6.4%, Fasting blood glucose of 100-125 mg/dL, and an oral glucose tolerance test (OGTT) 2 hour blood glucose of 140 mg/dL-199 mg/dL.

The term "Senescent leaf" refers to a leaf in senescence. Senescence is the last stage in the ontogenetic development of a leaf. Senescence is defined as a process of cellular elimination, which ends with the death of cells, tissues or organs. The end of senescence leads to the natural abscission of the leaf. Senescence and abscission respond to a strict genetic control, although they can also be produced by environmental adverse factors. The pattern of natural senescence is well established. Thus, the leaf cells first lose the integrity of the chloroplasts. The degradation of chlorophyll in leaf allows to see the pigmentation produced by the carotenoids. In addition, many plant species synthetize new carotenoids and other pigments of phenylpropanoid origin, such as anthocyanins and flavonoids that give new colors to the leaves before abscission. The activity of the nucleus is maintained until the end. Vascular tissues around the senescent body are the last to age, to ensure the transport of recycled nutrients. Synthesis of carbohydrates ends and takes place the degradation of proteins, chlorophylls, lipids and nucleic acids, which requires the synthesis of hydrolytic enzymes (proteases, nucleases, lipases and chlorophytases). Preferably senescent leaves are the abscised ones, but any leaf in the senescence stage can be used in the present invention.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention.

The following examples, drawings are provided by way of illustration and are not intended to be limiting of the present invention.

EXAMPLES

A study called PREDIABOLE has been carried out to demonstrate that the daily intake of 55 mL of the functional olive oil (oil enriched with oleanolic acid described in the present invention), will significantly reduce the incidence of DM2 in pre-diabetics, in comparison with those consuming the same olive oil not reinforced with the triterpene.
Research Design and Methods
Aim and Design of the PREDIABOLE Study The PREDIABOLE (PREvention of DIAbetes with OLEanolic acid) Study is a multicenter, randomized, double-blind, and controlled trial, designed as pilot study, and aimed to demonstrate that a dietary intervention based in the regular consumption of functional OA-enriched olive oil prevents DM2.

The hypothesis establishes that the daily intake of 55 mL of the functional olive oil, will significantly reduce the incidence of DM2 in pre-diabetics, in comparison with those consuming the same olive oil not reinforced with the triterpene. Thus, the primary outcome variable is the occurrence of diabetes, diagnosed according to the criteria of the American Diabetes Association (American Diabetes Association. Diagnosis and Classification of Diabetes Mellitus. Diabetes Care (2010) 33:Supplement 1, S1-S69).
Participants and Eligibility Eligible participants were community-dwelling women and men aged from 30 to 80 years, with overweight/obesity (BMI≥25 kg/m2), and diagnosed of IFG+IGT. IFG means fasting plasma glucose comprised between 5.6-6.9 mM, whereas IGT defined plasma glucoses in the range 7.8-11.1 mM, 2-hours after intaking a 75 g glucose preparation. All the participants provided written informed consent prior to be included in the study.

Individuals were not included in the trial if they were diabetics or treated with oral antidiabetic drugs or insulin, or reported a prediabetic history longer than seven years. People were also excluded if they had hypertriglyceridemia (fasting triglycerides>600 mg/dl) despite treatment, hypertension (systolic blood pressure 180 mmHg and/or diastolic blood pressure 110 mmHg), not-optimally treated thyroid disease, other endocrine diseases (such as Cushing's disease, acromegaly), or being in treatment against cancer. Neither were included people with syndrome of alcohol dependence or other type of addiction, nor whether they presented any physical, mental or intellectual limitation to participate in a study of dietary intervention, or showed difficulty or absence of predisposition to change their eating habits. Likewise, the existence of medical conditions or the use of drugs that interfere in the diagnosis of Diabetes (thiazide diuretics, beta blockers, systemic glucocorticoids, selective inhibitors of serotonin reuptake or other drugs for weight reduction) were exclusion criteria too. Similarly, were left out pregnant women, those who were going to plan their pregnancy during the study period, and those who were within 3 months postpartum or breastfeeding their babies.

Recruitment and Randomized Allocation

Participants were recruited among people assisted by 25 Primary Care Centers of the Andalusian Public System of Health (SAS) in the City of Seville (Spain). By mean of the computerized clinical histories (DIRAYA), family physicians identified candidates with at least two IFG values in the last 12 months, and invited them for a health screening to determine their eligibility. After an overnight fast, the candidates followed a selection process in the PREDIABOLE's reference center, which included the health history anamnesis, determination of height, weight and waist circumference, blood pressures measurement and a standard 75 g oral glucose tolerance test (OGTT) to quantify both the fasting plasma level and 2-h glycaemia. Individuals identified as prediabetics with IFG+IGT and with overweight/obesity were enrolled in the trial.

The study nurse assigned participants to one of the two study groups (intervention and control), using computer-generated random numbers for allocation. Four tables of randomization were built by sex and age (cut-off 60 years). The family physicians did not participate in the randomization process. The study nurses were independent of the nursing staff of the primary care centers. Therefore, they were not involved in the usual clinical care of participants, and their exclusive role was to collect data for the trial.

Elaboration and Characteristics of the Functional Olive Oil (Olive Oil Enriched with OA)

A commercial olive oil (a blend of virgin and refined olive oils) was selected by the researchers in the Instituto de la Grasa-CSIC, based in its minimal content of minor components (phenolics, sterols, tocopherols and triterpenoids) to avoid the masking of the OA biological activity. From this (control oil), a functional olive oil enriched at 600 mg OA/kg was elaborated by adding OA nanoparticles (97% purity) obtained from the OA crystals isolated from olive leaves according to the procedure described in the present invention.

In the PREDIABOLE Study, 10 batches of 500 L of both types of olive oils have been prepared (control and OA-enriched oils). In this document, by way of example, the different stages comprising the preparation of a representative batch of functional olive oil enriched in OA are described in detail.

1) Obtaining the Ethanolic Extract

The olive leaves are obtained from the pruning remains of the olive grove or from those accumulated in the oil mills after their separation from the olives.

Forty kilograms (40 kg) of olive leaf are dried to constant weight.

After washing with water and draining, the dry leaf (20.6 kg) is extracted by maceration with 412 L ethanol 96% (food grade) for 180 min, at a temperature between 23 and 25° C. The OA together with other compounds (fundamentally other triterpenes and phenolic compounds) present in the cuticle of the epidermis of the leaf are dissolved by alcohol.

The ethanolic extract (a total of 391 L) is separated from the olive leaf mass by filtration through Albet 240 paper.

The drying of the olive leaf reduces very significantly the content of pigments, and the introduction of an additional step of purification/decoloration of the extract by treatment with activated carbon (included in the Spanish Patent ES-2160553_B1) is not necessary.

2) Obtaining the Concentrate and Crystallization of the OA

The ethanolic extract is concentrated by vacuum distillation at 37-40° C. in ROTAVAPOR system, to obtain 80 L of concentrate. This concentration stage provides the thermodynamic driving force for the induction of the OA crystallization.

The crystallization is allowed to progress at rest for 36 hours at 20-25° C. To accelerate the nucleation and growth of the crystals, pure OA crystals are added to the concentrate as secondary nucleating agents.

The newly formed OA crystals are separated from the concentrate by filtration in a büchner funnel through Miracloth®.

Before separating the filter cake from the funnel, the crystals are washed with cold 96% ethanol (6-8° C.), for the elimination of traces of pigments and other possible contaminants.

The OA crystals thus obtained (335 g) have a purity of 95%.

Repetition of the concentration, crystallization and filtration steps allows to obtain another 179 g of OA, although with a lower purity (73-85%). Considered globally, the yield of the OA recovery from the olive leaf reaches 90.7%.

3) Heat Treatment of OA Crystals

The filter cake (purity 95%) is subjected to heat treatment in muffle at 165° C. for 20 min, increasing its purity up to 98%. Subsequently, the filter cakes are homogenized in a knife mill until a micronized powder is obtained.

4) Determination of the OA Purity

The purity of the OA obtained is determined by gas chromatography (GC-FID) and differential scanning calorimetry (DSC), following procedures developed in our laboratory (Spanish Patent ES-2160553_B1). For GC-FID analysis, due to the low volatility and high molecular weight of OA, prior derivatization by silanization is required. The silylating reagent is prepared by adding 3 mL of hexamethyldisilazane and 1 mL of trimethylchlorosilane to 9 mL of anhydrous pyridine. The solid OA obtained in point 3 is dissolved in absolute ethanol (0.5 mg/mL). To an aliquot of this OA solution (100 µL) 100 µL of a 0.5 mg/mL solution of 18β-glycyrrhetinic acid as internal standard is added, and the mixture placed in 1 mL gastight vials and evaporated to dryness under $N_2$ stream. The residue is dissolved in 200 µL of the silylating reagent and heated at 80° C. for 2 h.

After derivatization, an aliquot (1 µL) of the silylated solution is injected in an Agilent 6890N GC (Agilent Technologies, CA), equipped with a Rtx-65TG Crossbond capillary column (30 m; 0.25 mm ID; 0.1 mm film thickness) coated with 35% dimethyl-65% diphenyl polysiloxane as stationary phase (Restek, Co., Bellefonte, Pa.) and a FID detector. The injection is realized in split mode, and hydrogen is used as carrier gas (pressure at column head 140 kPa). The oven temperature is initially established at 260° C. for 9 min and programmed to increase up to 280° C. at a rate of 10° C./min and maintained at this value for 8 min. The injector and detector temperatures are isothermically established at 300° C. Under these chromatographic conditions the retention time of OA is 7.7 min. To obtain the melting thermogram, a differential scanning calorimeter Perkin-Elmer model DSC-4 was used. The sample is placed in sealed aluminum capsules and heated from 60° C. to 320° C. to 40° C./min. Indium is used as a standard for temperature calibration. The OA melting point determined under these conditions is 309° C.

5) Obtaining OA Nanoparticles

To prepare nanoparticles, the pulverized OA obtained in point 3 is processed in a Pulverisette 7 Premium Line planetary mill (FRITSCH GmbH, Idar-Oberstein, Germany), which operates for 2.5 cycles of 10 min at 500 rpm. Agate beads of 10 mm diameter are used. With this system, the 93.4% of the OA mass has a particle size distribution ($\mu \pm 3\sigma$) of 139.2±49.5 nm, whereas the remaining 6.6% consisting of aggregates of OA microparticles with sizes larger than 3000 nm.

6) Elaboration of Functional Olive Oil Enriched in OA

To 50 L of commercial olive oil (composition shown in Table 2) 280 g of the ground OA obtained in point 5 are added. The mixture is subjected to stirring for 1 minute in a blender, followed by ultrasonic treatment (180 W, 38° C. for 15 min). With this operation, a nanosuspension of OA in olive oil is obtained, with a triterpene concentration of 6087 mg/kg oil.

This nanosuspension is introduced in a stainless steel tank and 450 L of the same commercial olive oil are added. The mixture will remain in gentle agitation for 12 hours, at room temperature (22-25° C.).

In this way, the functional olive oil enriched in OA results in a final concentration of the bioactive compound of 608.7 mg/kg oil The chemical composition of the oils was characterized in the Instituto de la Grasa-CSIC by normalized methods. In addition, the Analytical Sensory Panel of the Instituto de la Grasa-CSIC determined their sensory profile, to ascertain that they could not be distinguish by their odor, taste or appearance.

Every six months new batches (500 L) of both control and functional olive oils were elaborated and bottled in 250 mL green-colored flasks. They were labelled with a six characters alphanumeric code for avoiding their identification. Researchers in the Instituto de la Grasa-CSIC managed the code sequence, and, therefore, participants, nurses and physicians were unaware of it.

Intervention and Follow-Up

The dietary intervention consisted in the intaking of 55 mL/day of the assigned oil (functional or control), distributed over the three meals (breakfast, lunch and dinner).

Participants were follow-up for up to 30 months from recruitment, according to a protocolled program of visits. At baseline and quarterly thereafter, participants received the allotment of the corresponding olive oil at no cost. Also at the quarterly visits, the study nurse performed anthropometric (height, weight and waist circumference) and blood pressure measurements in the participants, and also directed a short questionnaire about their lifestyle variables (diet, physical activity, and alcohol and tobacco consumption habits), medical conditions and use of medication. With this same periodicity, dietitians conducted individual and group dietary training sessions to provide information about healthy foods, meal plans, recipes and seasonal shopping lists; advising about the use of olive oil for cooking and dressing. They also recommended limiting the intake of fast/highly processed food, sweets, pastries, sugar-sweetened and alcoholic drinks.

At baseline and every six months afterwards, fasting blood samples were taken and analyzed for the serum glucose, insulin and HbA1c levels, as well as the lipid profile (triglycerides, total cholesterol, HDL-c and LDL-c). At each annual visit since the recruitment, participants were submitted to an OGTT. All these analytical determinations were made in the Laboratory of Analysis and Clinical Biochemistry of the 'Virgen del Rocio' University Hospital of Seville. In addition, aliquots of all the blood samples were sent to Instituto de la Grasa-CSIC to determine the plasma OA content. Laboratory technicians of both institutions were also blinded to the intervention groups.

Compliance to Allocation

Adherence to the dietary intervention has been assessed through two indirect methods: the self-reported compliance Haynes-Sackett (Rodriguez-Chamorro M A et al. Review of therapeutic compliance measurement tests used in clinical practice. *Atencion Primaria* 2008, 40, 413-417) test and the delivering of the empty bottles presumably consumed. In addition, the OA plasma levels have been measured, as objective biomarker of compliance, in a random sample of the PREDIABOLE biobank (25 aliquots per study group, corresponding to 0, 12, 18 and 30 months of follow-up).

Determination of Plasma OA

Plasma OA concentrations were determined according to the procedure described in the next document: Rada M. et al. GC-FID determination and pharmacokinetic studies of oleanolic acid in human serum. *Biomed. Chromatogr.* 2015; 29: 1687-1692. Briefly, 5 mL of serum were spiked with a known amount of betulinic acid (internal standard, IS), filtered through a cellulose acetate membrane (pore size 0.20 μm) and extracted with a mixture of 5% isopropyl alcohol in diethyl ether, followed by centrifugation at 3000 rpm for 10 min. The supernatant was concentrated to dryness by vacuum, and subsequently silanized with a mixture N,O-bis-(trimethylsilyl)trifluoroacetamide, trimethylchlorosilane, and pyridine. A one-microliter aliquot of the derivatized sample was analyzed by gas chromatography coupled to mass spectrometry detection (GC-MS). The identification of OA was accomplished by comparing the retention time and abundance ratios of two fragments ions (203 and 189 m/z). Its quantification was carried out based in the response factor respect IS.

Outcomes

The primary outcome of PREDIABOLE Study was the appearance of new diabetes cases, diagnosed according to the American Diabetes Association criteria stated at January 2010 (American Diabetes Association. Diagnosis and Classification of Diabetes Mellitus. Diabetes Care (2010) 33:Supplement 1, S1-S69). Explicitly, fasting plasma glucose with values higher than 7.0 mM; plasma glucoses above 11.2 mM, 2-h after a 75 g oral glucose load; or HbA1c≥6.5%.

When a new diabetes case was identified, a second test using the same criteria was required for its confirmation. The case ascertain was definitively done by the PREDIABOLE End-point Adjudication Committee, whose members were blinded to the allocation in the study groups. Once diabetes diagnosed, participants left out the study, and both they and their family doctors were informed to follow afterward the routine protocols for diabetes treatment.

As secondary outcomes data about the analytical determinations of blood parameters and other dependent variables have been obtained, such as the body mass index (BMI), pulse pressure [systolic (SBP)–diastolic (DBP) blood pressure], and the homeostasis model assessment [HOMA-IR=(insulimemia (μU/ml)×glycemia (mM))/22.5].

Adverse Effects

In each quarterly visit during the development of the trial, participants were questioned about the appearance of gastrointestinal disarrays or other kind of discomfort. On the other hand, a family physician not belonging to the study staff, and therefore being unaware of the allocation of the participants to the study groups, carried out a retrospective study using the electronic medical records.

She explored for each participant the period comprised between the inclusion in the trial up to two years after its completion, and focused on analytical values of serum creatinine levels (marker of renal function) and alanine and aspartate aminotransferase enzymes (as markers of hepatic alteration). Normal creatinine levels are established in 61.9 to 114.9 µM for men and 53 to 97.2 µM for women. A serum creatinine level 1.5-folds higher than the normal value (≈150 µM) was adopted as criteria of kidney function alteration. Likewise, plasma levels of hepatic enzymes alanine aminotransferase and aspartate aminotransferase (ALT and AST, respectively) vary depending on the weight and age of the person, and also from laboratory to laboratory, but the upper limit are always is established between 40 and 50 U/L. Values above 150 U/L suggest liver disease.

Since micro and macrovascular disorders are frequently associated to pathological complications of insulin resistance and diabetes, the electronic medical records were also explored for cerebral (transient ischemic stroke and ictus), cardiac (ischemic heart disease, chronic ischemia and effort angina) and peripheral (peripheral arterial disease) vascular diseases. In addition, any other significant adverse event suffered by participants were also took in consideration.

The End-point Adjudication Committee of the study confirmed the events reported by this family physician.

Ethics

The PREDIABOLE Study guaranteed the ethical principles commonly accepted in biomedical research with human beings: respect for the person and their autonomy. Participant were asked for the signed consent, after being informed of the objectives and methodology of the study, the activities in which they were involved, and the possible consequences—benefits and discomfort—that may appear due to their participation in the trial. In addition, participants were informed about restrictions on third parties in accessing data, the procedures to preserve confidentiality and the manner of publication of results.

The study also guaranteed the principles of non-maleficence (the priority will always be to cause no harm to the subjects), beneficence (the interventions would maximize the benefit for the participants), and justice (no individual who meets the inclusion requirements would be excluded depending on their age, sex, race or socioeconomic status).

The trial was conducted following the recommendations of the Helsinki Declaration and the requirements and guidelines of the Good Clinical Practice Guidelines of the International Conference on Harmonisation of Technical Requirements for Registration of Pharmaceuticals for Human Use (ICH).

The Bioethics and Research Committee of the Primary Care District Seville from SAS approved all the protocols at its session of May 5, 2010.

Statistical Analysis

Data analysis was done according to the intention-to-treat (ITT) principle. Descriptive statistics for qualitative variables was performed using absolute and relative frequencies (percentages). The quantitative variables were expressed by means and standard deviations (quantitative variables following a normal distribution) or as medians accompanied by IQR (variables not following a normal distribution). Comparisons between study groups for qualitative variables were done with the $\chi^2$ and the McNemar test, whereas the comparisons for quantitative variables were performed with the Student's t test or ANOVA.

It was fitted Cox regression models to assess the relative risk of diabetes by allocation group, estimating hazard ratios and 95% CIs. The time variable was the interval between randomization and the date of last follow-up or diabetes diagnosis, whichever occurred first. Participants who were free of diabetes or who were lost during follow-up were censored at the date of the last visit. Multiplicative interactions of the intervention with other variables were assessed using the likelihood ratio test for multiplicative product terms introduced in fully adjusted Cox models. The survival analysis, the probability of remaining free of diabetes during follow-up, was performed comparing the Kaplan-Meier survival curves by the log-rank method. All p values are two-tailed at $\alpha=0.05$. Statistical analysis were performed with SPSS (version 24.0; IBM SPSS Statistics, New York, USA) software.

Results

Eligibility/Recruitment and Baseline Characteristics of Population

Figure 2:
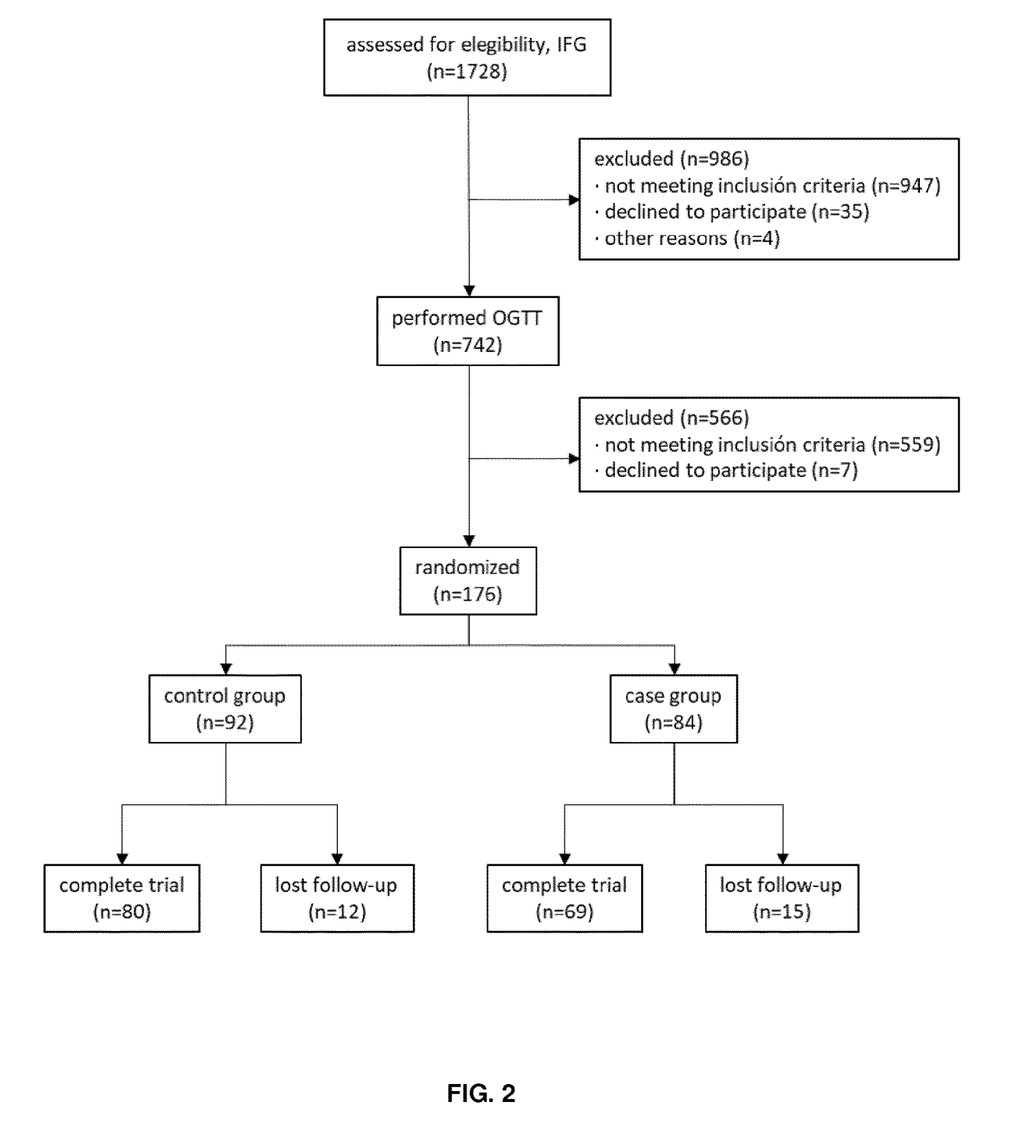
FIG. 2. Flow diagram of the study of the example provided below.

From June 2010 to September 2015, family doctors in 25 primary care centers in the city of Seville pointed 1728 potential participants diagnosed of IFG. Of these, 947 were left out during the selection process for not meeting the inclusion criteria and other 39 declined the invitation to participate. Therefore, 742 OGTT were performed, what identified 176 individuals who fulfilled the inclusion criteria with no exclusion conditions. They were randomly assigned to one of the two study groups, 92 to the control group and 84 to the intervention group (FIG. 2). Recruitment rate was slow by the difficulty to find individuals who fulfilled the inclusion and exclusion criteria. The baseline characteristics of individuals enrolled in the two study groups are shown in Table 1. The mean age of participants was determined in 67.6 years (95% CI 66.3-69.0), being women a 47.7% of them. Both groups were well balanced with respect to all the variables considered. In every item, the U test of Mann-Whitney-Wilcoxon compelled to retain the null hypothesis that both populations were identical at baseline.

TABLE 1

Baseline characteristics of the PREDIABOLE population

| | olive oil type | |
| --- | --- | --- |
| | control | OA enriched oil |
| n | 92 | 84 |
| age (years) | 67.4 ± 9.2 | 67.9 ± 9.0 |
| female sex (%) | 53.2 | 48.8 |
| weight (kg) | 81.7 ± 14.9 | 81.4 ± 15.1 |
| height (cm) | 162.7 ± 9.7 | 163.8 ± 10.2 |
| BMI (kg/cm$^2$) | 30.7 ± 4.2 | 30.1 ± 4.1 |
| waist circunference (cm) | 110.5 ± 10.2 | 108.1 ± 9.1 |
| SBP (mm hg) | 127.9 ± 15.7 | 130.2 ± 16.6 |
| DBP (mm hg) | 74.8 ± 9.3 | 75.8 ± 10.0 |
| plasma biomarkers | | |
| fasting glucose (mg/dL) | 112.5 ± 17.7 | 106.2 ± 14.6 |
| HbA1c | 6.0 ± 0.4 | 5.8 ± 0.5 |
| fasting insulin (µU/mL) | 15.4 ± 6.4 | 16.2 ± 5.2 |
| HOMA-IR | 4.3 ± 2.2 | 3.9 ± 2.3 |
| triglycerides (mg/dL) | 144.5 ± 63.1 | 141.3 ± 67.4 |
| total colesterol (mg/dL) | 204.0 ± 40.0 | 203.8 ± 36.1 |
| LDL-c (mg/dL) | 121.9 ± 33.8 | 121.9 ± 31.6 |
| HDL-c (mg/dL) | 54.7 ± 14.2 | 55.4 ± 17.5 |
| hs-CRP(mg/L) | 2.4 ± 2.0 | 2.4 ± 2.5 |

TABLE 1-continued

Baseline characteristics of the PREDIABOLE population

| | olive oil type | |
|---|---|---|
| | control | OA enriched oil |
| living habits | | |
| tobacco (cigarrette/day) | 20.1 ± 12.4 | 21.2 ± 16.3 |
| alcohol (units/week) | 9.6 ± 11.9 | 10.2 ± 14.2 |
| sedentary lifestyle (%) | 51.5 | 59.5 |
| family antecedent of dm2 | 57.6 | 48.8 |
| prediabetes evolution (months) | 22.3 ± 17.9 | 19.8 ± 18.2 |

Chemical Characterization of the OA-Enriched Olive Oil

Five bottles of each class of olive oil (control and functional) were randomly selected from each semiannually-elaborated oil batches, and analysed for their fatty acid composition, as well as the phenolics, sterols, tocopherols and triterpenoids contents. Total contents of chlorophills and carotenoids were also determined. In addition, the quality indexes (acidity, peroxide value and ultraviolet absorbance coefficients at 232 and 270 nm) were measured. A representative composition of both types of olive oils is shown in Table 2.

TABLE 2

Typical chemical composition of the olive oil used in the study

| Component | |
|---|---|
| free acidity (% oleic acid) | 0.37 ± 0.02 |
| peroxide value (meq o$_2$/kg oil) | 3.39 ± 0.02 |
| $k_{232}$ | 1.82 ± 0.17 |
| $k_{270}$ | 0.29 ± 0.00 |
| fatty acids (%) | |
| palmitic (16:0) | 10.4 ± 0.3 |
| palmitoleic (16:1 n-7) | 0.8 ± 0.0 |
| estearic (18:0) | 3.4 ± 0.1 |
| oleic (18:1 n-9) | 77.4 ± 0.1 |
| linoleic (18:2, n-6) | 5.8 ± 0.0 |
| α-linolenic (18:3 n-3) | 0.3 ± 0.1 |
| arachidic (20:0) | 0.4 ± 0.1 |
| gadoleic (20:1 n-11) | 0.7 ± 0.0 |
| total phenolics (µg/g oil) | 62.4 ± 0.7 |
| hydroxytyrosol and derivatives | 21.7 ± 0.2 |
| tyrosol and derivatives | 39.8 ± 0.2 |
| lignanes | 0.5 ± 0.0 |
| flavonoids | 0.3 ± 0.0 |
| simple phenols | 0.0 ± 0.0 |
| total sterols (µg/g oil) | 1409.3 ± 4.6 |
| β-sitosterol | 1223.0 ± 2.1 |
| δ5-avenasterol | 50.6 ± 0.9 |
| campesterol | 47.9 ± 0.1 |
| stigmasterol | 12.7 ± 0.0 |
| clerosterol | 15.5 ± 0.0 |
| δ5,24-stigmastadienol | 16.2 ± 0.7 |
| δ5,23-stigmastadienol | 9.9 ± 0.0 |
| total tocopherols (µg/g oil) | 270.8 ± 4.4 |
| α-tocopherol | 236.7 ± 0.7 |
| triterpenoids (µg/g oil) | |
| erythrodiol | 40.9 ± 0.1 |
| uvaol | 3.5 ± 0.7 |
| oleanolic acid (control/enriched oils) | 3.9 ± 0.1/ 608.7 ± 30.4 |
| maslinic acid | 4.6 ± 0.2 |
| total chlorophills (µg/g oil) | 1.3 ± 0.1 |
| total carotenoids (µg/g oil) | 1.4 ± 0.0 |

Follow-Up and Compliance to Allocation

Participants in the study were followed for a median of 27.5 months (IQR 13.3-30.0). The distribution of follow-up times in the two study groups [medians 25.0 (12.0-30.0) for the control group and 30.0 (15.0-30.0) for the intervention group] were equal according to the U-test.

The adherence to the dietary intervention was high and similar in the two study groups, as assessed through two indirect methods: the self-reported compliance Haynes-Sackett test and the delivering of the empty bottles presumably consumed. The plasma levels of OA, also suggests good compliance with the allocation group (Table 3).

TABLE 3

Oleanolic acid levels in fasting plasmas of a 25 individuals cohort of each study group. Data are expressed as mean ± SD

| Follow-up | control oil | OA-enriched |
|---|---|---|
| 0 | 165.4 ± 43.3 | 157.1 ± 50.9 |
| 12 | 179.9 ± 84.8 | 193.2 ± 125.6 |
| 18 | 218.9 ± 102.9 | 215 ± 126.1 |
| 30 | 266.2 ± 104 0 | 306 ± 213.6 |

The fasting OA plasma concentrations showed a clear trending of increase along the trial progression, although this was not translated in significant differences (one way ANOVA test p<0.05) between study groups, nor within an allocation group when the follow-up time increased.

Along the trial a total of 27 dropouts were recorded, 12 in the control group (13.0%) and 15 in that of intervention (17.9%) (FIG. 2). The characteristics of these individuals were no different of those who completed the trial, not suggesting the existence of differences that could become confounding factors in the analysis of results.

End-Points

During the follow-up period, 48 participants developed diabetes (events), 31 in the control group and 17 in the intervention one (Table 4).

TABLE 4

Incidence of diabetes and hazard ratios by study groups. Cox regression models were used to assess the relative risk of diabetes by allocation group, estimating hazard ratios and 95% CI.

| | OA-enriched oil | control oil | p value |
|---|---|---|---|
| participants | | | |
| n | 84 | 92 | |
| person-months of follow-up | 1923 | 1903 | |
| events | | | |
| new DM2 onset | 17 | 31 | |
| incidence rate per 1000 | 8.8 | 16.3 | |
| persons-months (95% CI) | (5.1-14.2) | (11.1-23.1) | |
| hazard ratio for (95% CI) | | | |
| crude model (oil type) | 0.533 (0.289-0.981) | 1 (ref.) | 0.043 |
| multivariable adjusted model† | 0.485 (0.266-0.882) | 1 (ref.) | 0.018 |

†Additionally adjusted for insulin resistance (HOMA-IR) and hypercholesterolemia, assuming both variables as categoric: HOMA-IR ≥ 3.8 and TC ≥ 200 mg/dL.

These mean that incidence rate of diabetes for the control group almost doubled that for the intervention group, respectively. This is also supported by an unadjusted hazard ratio of 0.533 (0.289-0.981) for the intervention group as compared with the control one, a difference found as significative (p=0.043) by the likelihood ratio test for the overall effect of the intervention. After adjustment for potential confounders (insulin resistance and hypercholesterolemia), the hazard ratio was 0.485 (CI 0.266 to 0.882), indicating a 51.1% reduction of the relative risk of incident diabetes in the study group consuming the OA-enriched functional olive oil as compared with the group intaking the control oil. In multivariable Cox's regression models, sex, age, BMI, sedentary lifestyle, LDL-c, HDL-c, tobacco and alcohol addictions, were unrelated to the intervention effect on the progression to diabetes.

Figure 3:
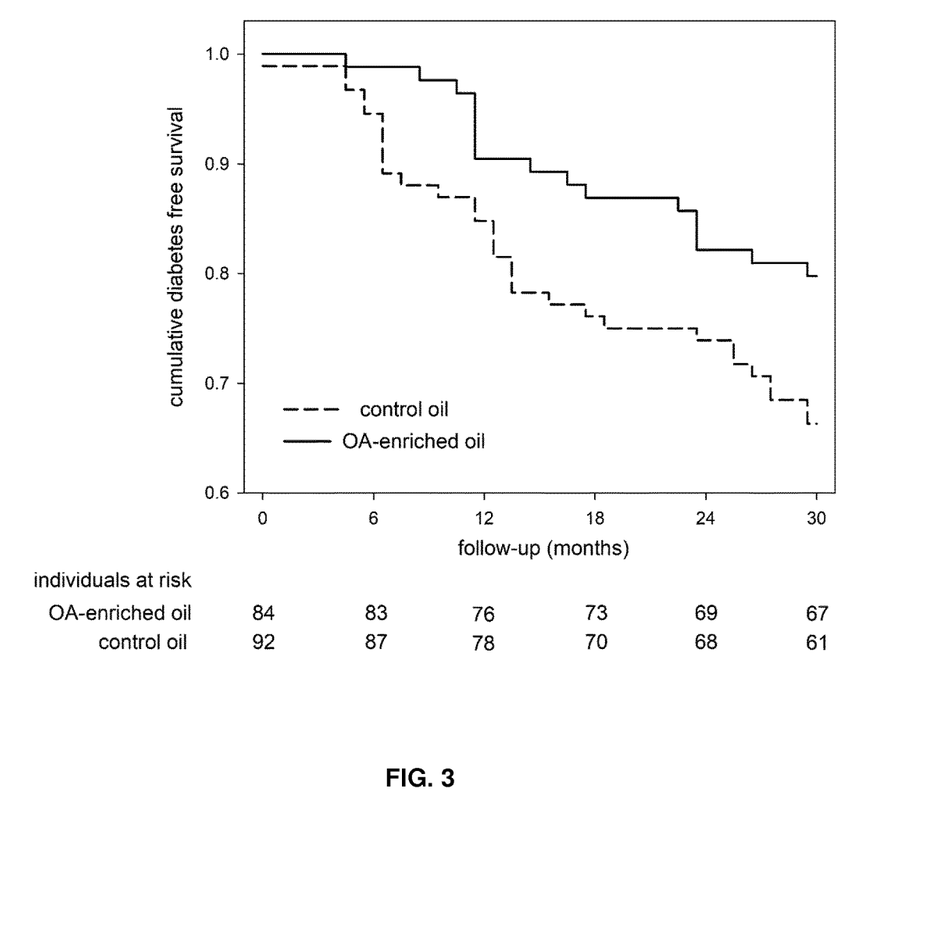
FIG. 3. Cumulative diabetes free survival curves obtained in the example provided below. Cox regression model with outcome of diabetes onset and exposure to the OA-enriched oil intervention versus the control olive oil

The Kaplan-Meier curves for the cumulative diabetes free survival was lower in the control group in comparison with the OA-enriched one, and diverged very clearly since the onset of the trial. The free survival time was estimated for both study groups and expressed as mean±SE and 95% CI, resulting 24.3±1.0 (22.3-26.2) months, for the control group and 27.0±0.8 (25.5-28.5) months for the intervention group. This outcome was determined as statistically different by the log rank test of equality of survival distributions (Chi-square 4.315; p value 0.038) (FIG. 3).

Adverse Effects

During the development of the clinical trial, no participant reported gastrointestinal intolerance (including nausea, flatulence, abdominal pain or alteration of the depositional habit) or any other type of discomfort. On the other hand, the retrospective study of the electronic medical records of participants allowed identify significant finding in ten individuals (seven in the control group and three in the OA-enriched group) (Table XX). Two of them (one in the control group and the other in the OA-enriched functional olive oil group) already displayed antecedents of vascular diseases before their recruitment in the trial.

TABLE 5

Individuals with significant disorders, appearing during their participation in the trial (during) and the two years after their completion(post).

| case | group | finding | period | other finding | antecedents | death |
|---|---|---|---|---|---|---|
| 1 | control | elevated ALT + AST | post- | cancer (lung) | – | + |
| 2 | control | transient ischemic cerebral stroke | post- | – | – | – |
| 3 | control | ischemic heart disease | post- | – | – | – |
| 4 | control | elevated creatinine | post- | cancer (bladder) | ischemic heart disease | – |
| 5 | control | ictus | during | – | – | – |
| 6 | control | ischemic heart disease | during and post | angina | – | – |
| 7 | control | peripheral arterial disease | post- | – | – | – |
| 8 | OA-enriched | elevated creatinine elevated ALT + AST | during post- | cancer (lung) | – | – |
| 9 | OA-enriched | chronic ischemia | post- | – | transient ischemic stroke | – |
| 10 | OA-enriched | effort angina | during | – | – | – |

In consequence, attending to the findings of this preliminary study it could be held that the administration of the OA-enriched functional olive oil, at the indicated daily dose, for at least 30 months, is safe for humans.

DISCUSSION

The increasing demand for natural products as alternative therapies for chronic diseases, encouraged research into the pharmacological importance of plant bioactive compounds. Given the accumulated evidence of the therapeutic potential of OA in experimental models, there is a clear indication that, if fully explored, OA offers promising alternatives in the management of diabetes and its complications in humans. Despite this, data in literature on the use of OA in clinical trials and therapies are very scarce. The supposed poor bioavailability of the triterpene has probably diverted the efforts towards the chemical modification of the OA molecule to achieve non-toxic, more potent and bioavailable synthetic derivatives. Although some of them, as Bardoxolone-Me, showed promising therapeutics effects [Wang Y-Y, Yang Y-X, Zhe H, He Z-X, Zhou S-F. Bardoxolone methyl (CDDO-Me) as a therapeutic agent: An update on its pharmacokinetic and pharmacodynamic properties. Drug Design, Development and Therapy 2014, 8, 2075-2088] their safety is questioned nowadays (de Zeeuw D, Akizawa T, Audhya P, Bakris G L, Chin M, Christ-Schmidt H, Goldsberry A, Houser M, Krauth M, Lambers-Heerspink H J, McMurray J J, Meyer C J, Parving H-H, Remuzzi G, Toto R D, Vaziri N D, Wanner C, Wittes J, Wrolstad D, Chertow G M. Bardoxolone methyl in type 2 diabetes and stage 4 chronic kidney disease. N. Engl. J. Med. 2013, 369, 2492-2503).

Now, with the PREDIABOLE Study, it is claimed the therapeutic utility in humans of the OA of natural origin, not chemically modified, obtained from the olive leaf, and in absence of adverse effects. This research on this triterpene has let the applicant to describe procedures to obtain high purity OA nanoparticles and to elaborate an OA-enriched functional olive oil, a formulation in which the triterpene exhibits the highest bioavailability reported until now (Rada M. et al. GC-FID determination and pharmacokinetic studies of oleanolic acid in human serum. *Biomed. Chromatogr.* 2015; 29: 1687-1692).

The PREDIABOLE Study demonstrates that a long-term intervention with an OA-enriched functional olive oil may reduce the incidence of diabetes in people at high risk to develop it (IFG+IGT). After a median 27.5 months follow-up, a statistically significant 51.5% relative risk reduction in individuals intaking the OA-enriched olive oil was observed, in comparison with those consuming the control oil. This effect is exclusively attributable to the presence of therapeutic concentrations of OA, since no other change in lifestyle was implemented differentially in the intervention group with respect to the control one. Recommendations on the overall composition of the dietary pattern, increased physical activity, weight loss, moderate consumption of alcohol or avoiding the use of tobacco, were given to both study groups in an identical manner.

These considerations were corroborated by the regression logistic models (table 4).

The PREDIABOLE Study also validates that the long-term administration of high concentrations of the natural OA (36 mg/day for up to 30 months) is safe for humans (Table 5). As a reference, solid micronized OA (20 mg/capsule) is currently under commercialization in the People's Republic of China for treatment of liver diseases, without having transcended, to inventors' knowledge, unfavourable effects worthy of mention. It should be mentioned that micronized OA is endowed with a low bioavailability, at difference with the OA-enriched functional olive oil subject of this invention.

The secret of a successful clinical trial is compliance. In PREDIABOLE Study, data were analysed according to the ITT principle, which records data of all subjects after randomization, regardless of their compliance with the protocols. This allows keeping the randomization until the end of the study, decreasing the probability of biasing the results. The adherence to the dietary intervention in PREDIABOLE was high, as assessed by the Haynes-Sackett test (Rodriguez-Chamorro M A. et al. Review of therapeutic compliance measurement tests used in clinical practice. *Atención Primaria* 2008, 40, 413-417), and by the delivery of the empty bottles presumably consumed. The analysis of plasma levels of OA, as objective biomarker, also suggests good compliance (Table 3). The fasting OA plasma concentrations showed a consistent trending of increase along the trial progression, with average values of ca. 160 ng/mL at the onset of the study and 300 ng/mL, approximately, after 30 months of follow-up, although this was not translated in significant differences (one way ANOVA test p<0.05) between study groups, nor within an allocation group when the follow-up time increased.

In the previous pharmacokinetics study of the inventiors (Rada M. et al. GC-FID determination and pharmacokinetic studies of oleanolic acid in human serum. *Biomed. Chromatogr.* 2015; 29: 1687-1692) they determined that the mean residence time of OA in human blood after its ingestion is 8.9 hours. Consequently, the OA plasma concentrations after fasting overnight should correspond to its baseline values, since it was the only moment in which participants were out of the postprandial phase. Effectively, the inventors' data are similar to those reported in Rada et al., once completed the clearance of the triterpene. The increased adherence to a healthy diet, rich in fruits and vegetables, and with an moderate-high consumption of olive oil, as result of recommendations offered by the dietitians, could explain the increase in the basal OA levels of all the participants, independently of the allocation group.

The formulation used for administering OA, an olive oil, has been other important aspect that may explain the high acceptability of the trial and compliance. Although, this fatty formulation could be considered inadequate by hypercaloric to combat obesity, insulin resistance and diabetes, studies performed in the last two decades have revealed that the Mediterranean diet, moderately rich in fat (35-40% of energy), in which olive oil plays a key role, is a healthy dietary pattern. Recently, Schwingshackl and collaborators performed a meta-analysis of four cohort studies and 29 randomized controlled trials on the effects of olive oil-enriched diets on risk of DM2 (Schwingshackl L, Lampousi A-M, Portillo M P, Romaguera D, Hoffmann G, Boeing H. Olive oil in the prevention and management of type 2 diabetes mellitus: a systematic review and meta-analysis of cohort studies and intervention trials. Nutrition & Diabetes (2017) 7, e262; doi:10.1038/nutd.2017.12). Their analysis associated olive oil intake with a decreased risk to develop DM2 in healthy individuals and an improved glucose metabolism in patients with already established diabetes. The PREDIMED Study, a randomized trial done in Spain (2003-2009) with people at high risk of cardiovascular disease, demonstrated that a long-term intervention with a Mediterranean diet reinforced in virgin olive oil (50 mL/day) reduced the incidence of major cardiovascular events (Estruch R, Ros E, Salas-Salvadó J, Covas M I, Corella D, Arós F, Gomez-Gracia E, Ruiz-Gutiérrez V, Fiol M, Lapetra J, Lamuela-Raventos R M, Serra-Majem L, Pintó X, Basora J, Muñoz MA, Sorlí JV, Martinez J A, Martínez-González M A, et al. Primary Prevention of cardiovascular disease with a Mediterranean diet. N. Eng. J. Med. 2013, 368, 1279-1290), and causes a significant 40% reduction of the relative risk for diabetes (Salas-Salvadó J, Bulló M, Estruch R, Ros E, Covas M I, Ibarrola-Jurado M, Corella D, Arós F, Gómez-Gracia E, Ruiz-Gutiérrez V, Romaguera D, Lapetra J, Lamuela-Raventós R M, Serra-Majem L, Pintó X, Basora J, Muñoz MA, Sorlí JV, Martínez-González MA. Prevention of Diabetes With Mediterranean Diets. Annals of Internal Medicine 2014, 160:1-10), in comparison with a low-fat control diet. These studies were majorly implemented using virgin olive oil, and explained antidiabetic effects by the high content of oleic acid and also by the presence of secoiridoids, such as oleuropein and hydroxytyrosol. Therefore, they overlooked the biological activity of other bioactive compounds naturally present in olive oils and other Mediterranean foods, as pentacyclic triterpenoids.

The improvement of glucose homeostasis, lipid metabolism and insulin signalling, and the reinforcement of the adaptive cell response to oxidative stress and inflammation, are well recognised pharmacological features of OA in experimental models (Castellano J M, Guinda A, Delgado T, Rada M, Cayuela J A. Biochemical Basis of the Antidiabetic Activity of Oleanolic Acid and Related Pentacyclic Triterpenes. Diabetes 2013, 62, 1791-1799). In addition, OA lacks adipogenic activity, what make it a promising biomolecule, potentially better than most commonly used antidiabetic agents that usually display some adverse effects and often lead to weight gain (Sung H Y, Kang S W, Kim J L, Li J, Lee E S, Gong J H, Han S J, Kang Y H. Oleanolic acid reduces markers of differentiation in 3T3-L1 adipocytes. Nutr. Res. 2010, 30, 831-839).

Limitations and Strengths

The PREDIABOLE study has some limitations. First, since it involves a dietary intervention in autonomous adults with normal social lives, inventors cannot absolutely guarantee that they strictly followed the requiring consumption of olive oil nor the given recommendations. As identification of potentially non-compliant individuals during recruitment is crucial, inventors used pre-randomization interview models that proved to choose people with good predisposition to change lifestyle and high probability of being compliant with the protocols. All the parameters inventors used to assess compliance indicate that this was excellent. Second, the target population consisted of adults at high risk of diabetes (IFG+IGT), what could limit the generalizability of the results to younger people or individuals less exposed to the disease progression. Third, inventors had slight greater losses during follow-up in the intervention group than in the control one. However, the high homogeneity in the baseline characteristics of participants does not suggest that this may biases the results. Moreover, losses maintained below 20% of participants, a percentage well accepted in the design of similar trials. In any case, this difference could be undervaluing diabetes incidence in the control group, and, therefore, undervaluing the OA benefits. The ITT approach demands an adequate follow-up of participants, since the greater the dropouts, the greater the threat to the validity of results. In this sense, the nurses and doctors of PREDIABOLE performed a close follow-up of participants using all means at their fingertips (reminders by family doctors, e-mailing, phoning, etc.).

The study also has strengths. Its randomized design resulted in study groups very well balanced for potential sources of confounding, able to provide first-line evidence in supporting a causal association between OA administration and diabetes prevention. This is a considerable advantage over observational studies assessing the relationship between adherence to dietary patterns through questionnaires and diabetes incidence.

Other strength is the absolute observance of the double-blind design, in which participants and health personnel (including members of the End-point Adjudication Committee) were unaware of the oil type assigned to the study groups. The alphanumeric code sequence was exclusively known by the IG-CSIC researchers. This is also an important improvement over studies such as PREDIMED in which the blinding was not feasible in the feeding-type allocation.

Another factor constituting a strength of PREDIABOLE that consolidates the antidiabetic effect of OA in humans, is the formulation chosen for the triterpene vehiculization. Instead comparing the effect of the intervention versus a placebo or, as more frequently, a low-fat diet, inventorshas contrasted their hypothesis using as control a Mediterranean type diet reinforced with olive oil, which has already revealed as effective in the prevention of DM2. The presence of therapeutic concentrations of OA in the PREDIABOLE functional olive oil has pharmacological potential to reduce an additional 51% the relative risk of developing DM2 in individuals at high risk. On the other hand, PREDIABOLE performed a long term administration of high-dose of OA, controlling of a number of variables associated with metabolic syndrome and diabetes, which is pioneer, at inventors' understanding, in humans.

Precepts of evidence-based medicine require providing high-level scientific evidence before nutritional recommendations for whole population can be formulated. Although basic research is useful in understanding the action mechanisms of biocompounds, this evidence is obtained from randomized clinical trials and cohort studies. The level of evidence of a particular study depends not only on its design, but also on its quality. The PREDIABOLE Study is a fully randomized, controlled, double-blind pilot trial, well designed and executed, which provides strong evidence that long-term consumption of an OA-enriched olive oil results in a substantial reduction in the risk for DM2. The dietary intervention supported by PREDIABOLE is in addition safe and palatable. Therefore, it has high potential for being long-term sustainability. Thus, PREDIABOLE illustrates cumulated evidence that lifestyle interventions can reduce incidence of diabetes and other related pathologies. The dramatic increment of diabetes prevalence since the beginning of the XXI Century, demands from the national health systems to introduce urgent preventive measures that delay or avoid the appearance of the disease, but also the implementation of combined therapies in more advanced stages of its progression. The use of functional foods containing natural OA is, undoubtedly, an interesting alternative.

Further investigations are needed to consolidate the PREDIABOLE evidence and extend the use of natural triterpenes in the design of new drugs and foods, which allow personalized diets and nutrigenomic approaches for the prevention of high-prevalence chronic disorders such as diabetes, cancer, or neurodegenerative and cardiovascular diseases.

The invention claimed is:

1. An olive oil comprising a starting olive oil enriched with crystalized oleanolic acid (OA) characterized in that a concentration of the crystalized oleanolic acid in said starting olive oil, including the crystalized oleanolic acid formed as glycosylated derivatives and esters, is comprised between 580 and 650 mg/kg, wherein the starting olive oil is virgin olive oil, extra virgin olive oil, refined olive oil or mixtures thereof, wherein the crystalized OA comprises OA nanoparticles having a size between 90 and 300 nm at a concentration between 6000 and 6600 mg/kg, wherein the OA nanoparticles exist in a diluted volume ratio of a nanosuspension to the starting olive oil being between 1:7 and 1:15.

2. A process to obtain the olive oil enriched with crystalized oleanolic acid (OA) according to claim 1, wherein the process comprises at least the following steps:
   1) Grinding the crystalized OA to produce the OA nanoparticles,
   2) Adding the OA nanoparticles to a portion of starting olive oil to a concentration between 6000 and 6600 mg/kg to form a nanosuspension,
   3) Submitting the nanosuspension to treatment by ultrasounds,
   4) Diluting the nanosuspension to a ratio of between 1:7 and 1:15 with the starting olive oil, and
   5) Stirring the diluted solution of crystalized OA in the starting olive oil at room temperature for between 10 and 15 hours;
   wherein the crystalized OA is obtained by a method comprising:
   a) extracting oleanolic acid from the leaves of *Olea europaea* by contacting the leaves of *Olea europaea* with an organic solvent for between 30 and 240 minutes in a leaf/solvent ratio of between $1/10$-$1/50$ weight/volume and at a temperature of between 20-70° C.;
   b) filtering the extract obtained in step a);
   c) concentrating the filtrate obtained in step b) by evaporating the solvent until achieving a volume of between 5% and 20% of the initial one before concentration;
   d) applying fractioned crystallization at room temperature, and separation of OA crystals by filtration; and
   e) drying the crystalized solid separated in step d) for a period of time of between 5 and 30 minutes and at a temperature of between 130° C. and 220° C.

3. The process according to claim 2, wherein the grinding is carried out for 2.5 cycles of 10 min at 500 rpm in a planetary micro mill, equipped with agate balls of 5-10 mm diameter.

4. The process according to claim 3, wherein between 70-95% by weight in relation to a total weight of the grinded OA nanoparticles obtained in the grinding step have an average particle size between 90-300 nm.

5. The process according to claim 2, wherein the leaves of *Olea europaea* used in step a) to obtain the crystalized OA are senescent dry leaves.

6. The process according to claim 2, wherein the ultrasounds of step 3) are carried out at 180 W, 38 QC for 15 min.

7. The process according to claim 2, wherein the step 3) is carried out without surfactants.

8. A method of using the olive oil enriched with crystalized oleanolic acid according to claim 1, wherein the olive oil enriched with crystalized oleanolic acid is used in the treatment of Diabetes Mellitus type 2 and in the treatment of pre-diabetes.

9. The method of using the olive oil enriched with crystalized oleanolic acid according to claim 8, wherein the olive oil enriched with crystalized oleanolic acid is administrated to a subject at a daily dose between 45 and 65 ml.

10. A pharmaceutical composition comprising the olive oil enriched with crystalized oleanolic acid according to claim 1.

11. A food composition comprising the olive oil enriched with crystalized oleanolic acid according to claim 1.

* * * * *